(12) United States Patent
Yang et al.

(10) Patent No.: US 12,370,236 B2
(45) Date of Patent: Jul. 29, 2025

(54) METHOD AND COMBINATION FOR THE SUPPRESSION OF COVID-19 VIRUS

(71) Applicants: National Tsing Hua University, Hsinchu (TW); Praexisio Taiwan Inc., New Taipei (TW)

(72) Inventors: Lee-Wei Yang, Garland, TX (US); Kun-Lin Tsai, Hsinchu (TW); Bang-Chieh Huang, Taipei (TW); Yi-Yun Cheng, Hsinchu (TW); Sui-Yuan Chang, Taipei (TW)

(73) Assignees: NATIONAL TSING HUA UNIVERSITY, Hsinchu (TW); PRAEXISIO TAIWAN, INC., New Taipei (TW)

( * ) Notice: Subject to any disclaimer, the term of this patent is extended or adjusted under 35 U.S.C. 154(b) by 0 days.

(21) Appl. No.: 18/048,262

(22) Filed: Oct. 20, 2022

(65) Prior Publication Data

US 2023/0122049 A1 Apr. 20, 2023

Related U.S. Application Data

(60) Provisional application No. 63/257,657, filed on Oct. 20, 2021.

(51) Int. Cl.
| | | |
|---|---|---|
| *A61K 38/14* | (2006.01) | |
| *A61K 31/4015* | (2006.01) | |
| *A61K 31/403* | (2006.01) | |
| *A61K 31/472* | (2006.01) | |
| *A61K 31/496* | (2006.01) | |
| *A61P 31/14* | (2006.01) | |

(52) U.S. Cl.
CPC .......... *A61K 38/14* (2013.01); *A61K 31/4015* (2013.01); *A61K 31/403* (2013.01); *A61K 31/472* (2013.01); *A61K 31/496* (2013.01); *A61P 31/14* (2018.01)

(58) Field of Classification Search
None
See application file for complete search history.

(56) References Cited

PUBLICATIONS

Bhat et al. ("Targeting allosteric pockets of SARS-CoV-2 main protease Mpro," Journal of Biomolecular Structure and Dynamics (2022), 40(14), 6603-6618, published Feb. 27, 2021) (Year: 2021).*
Eberle et al. ("The Repurposed Drugs Suramin and Quinacrine Cooperatively Inhibit SARS-CoV-2 3CLpro In Vitro," Viruses 2021, 13, 873, pp. 1-21, published May 10, 2021) (Year: 2021).*
Fu et al. ("Both Boceprevir and GC376 efficaciously inhibit SARS-CoV-2 by targeting its main protease," Nature Communications (2020) 11:4417, pp. 1-8) (Year: 2020).*
Stone et al. Potential for Interactions between Caspofungin and Nelfinavir or Rifampin, Antimicrobial Agents and Chemotherapy, Nov. 2004, p. 4306â4314) (Year: 2004).*

* cited by examiner

*Primary Examiner* — Christina Bradley
(74) *Attorney, Agent, or Firm* — HSML P. C.

(57) ABSTRACT

Provided is a method for treating a SARS-CoV2 $3CL^{pro}$-related disease in a subject in need thereof by blocking dimerization of 3C-like main protease ($3CL^{pro}$) of the SARS-CoV2, including administering to the subject a first agent which binds to a first binding site of a SARS-CoV2 $3CL^{pro}$ complex and a second agent which binds to a second binding site of the SARS-CoV2 $3CL^{pro}$ complex, wherein the first binding site and the second binding site are functionally different sites in the three-dimensional structure of the SARS-CoV2 $3CL^{pro}$ complex. Also provided is a pharmaceutical combination including the first agent and the second agent for suppressing SARS-CoV2, thereby alleviating COVID-19.

17 Claims, 6 Drawing Sheets

METHOD AND COMBINATION FOR THE SUPPRESSION OF COVID-19 VIRUS

TECHNICAL FIELD

The present disclosure relates to improved therapeutic regimens for treating COVID-19, and more particularly, to compounds and methods for blocking dimerization of 3C-like main protease of COVID-19 virus, and combined uses of active site inhibitors and interface blockers that may additively or synergistically suppress COVID-19 virus.

BACKGROUND

COVID-19 pandemic, caused by SARS-CoV2, has caused unforeseen global health crisis since the beginning of 2020. The fastest remedy to save lives who are seriously infected thus far has been the repurposed FDA drugs originally targeting other diseases or other viruses. To conquer the crisis, one of the approaches is to inhibit the function of the SARS-CoV2 3C-like main protease ($3CL^{pro}$) which controls the replication of the COVID-19 virus. There have been a number of studies that focus on developing the active site inhibitors of $3CL^{pro}$ (Chen et al., 2021, Nucleic Acids Research, 49, D1152-D1159; Zhang et al., 2020, Science, 368, 409-412; Pathak et al., 2021, ACS Nano, 15, 857-872). According to recent studies, the $3CL^{pro}$ is enzymatically active only in its dimeric form, while it is inactive in monomeric form (Shi et al., 2008, J. Virol. 82, 4620-4629; Lim et al., 2019, Prog. Biophys. Mol. Biol., 143, 52-66). Understanding such a regulatory nature, it can be a tempting therapeutic strategy to develop interface blockers to prevent the interaction between two $3CL^{pro}$ monomers.

Designing drugs specifically targeting at protein-protein interface (PPI) has become a drug development strategy receiving high attention. At present, there have been successful cases of drug development in the field of immunology. By targeting tumor necrosis factor-α (TNF-α) and its receptor PPI in tumors, five FDA-approved drugs have been found to inhibit their biochemical reactions (Palladino et al., 2003, Nature Reviews Drug Discovery, 2, 736-746; Tansey et al., 2009, Drug Discovery Today, 14, 1082-1088). In addition, there have been 6 FDA-approved drugs reported to inhibit the PPI between adenylyl cyclase type 8 (AC8) and calmodulin (CaM) (Hayes et al., 2018, ACS Chem. Neurosci., 9, 346-357). In fact, the design of PPI blockers requires some prerequisites; for example, the buried surface area (BSA) of the PPI does not exceed 4,000 Å2 (Ran et al., 2018, Curr. Opin. Chem. Biol., 44, 75-86). Generally, the PPI of a protein that is too large or that has a smooth interface is easily regarded as "undruggable" (Ran et al., 2018, Curr. Opin. Chem. Biol., 44, 75-86). In the past, researchers used computer docking technology analysis to dock a large number of different small molecules as probes on the surface of a protein, and then classified the position of each docking result to find the "druggable" hot spots belonging to this protein for future medications.

Nevertheless, there is still an unmet need to identify competent medications that have potential to effectively treat COVID-19, e.g., targeting the interface of SARS-CoV2's essential proteins.

SUMMARY

The present disclosure provides a concept aiming to use a pharmaceutical combination of at least two active ingredients to target more than two potential druggable sites in a single protein target. The concept can promote the drug repurposing, and by the pharmaceutical combination of multiple moderate to weak binders, the dosage and thus the toxicity of each drug can be reduced while achieving a similar or better therapeutic effect. The strategy can ideally apply to any protein target, given the druggable protein-protein interfaces or allosteric sites available, and it can also promote the exhaustive use of the available chemical space to regulate known or new protein targets for human diseases and other emerging infectious diseases.

The protein-protein interface can be identified by both experimental techniques, such as X-ray crystallography and the chemical shift perturbation data based on nuclear magnetic resonance (NMR) spectroscopy, and computational methods, such as protein-protein docking and molecular dynamics (MD) simulations. The identification of allosteric sites could require mutation screening for protein function. In addition, computational methods, such as time-dependent and independent linear response theory (LRT), model the atomic displacement inside correlated atomic motion upon remote perturbation, and thus can probe frequently communicating residues, e.g., allosteric sites. Furthermore, MD simulation and elastic network models can extend the conformational space for ensemble structure screening to enrich more effective drugs that would not be all found using a single protein conformation. With the alternative druggable sites and ensemble structures, the present disclosure provides a general framework for designing therapeutics to drug more than one site in new or known disease-related protein targets.

The allosteric regulation is the activity modulation of an enzyme by binding an effector molecule at a site other than the enzyme's active site. An allosteric inhibitor by binding to an allosteric site alters the protein conformation and/or dynamics in the active site of an enzyme. As a result, the enzyme no longer well binds to its specific substrate and thus loses its catalytic activity, i.e., the enzyme is now inactive.

Protein-protein interactions may occur between identical or non-identical chains (i.e., homo- or hetero-oligomers). Different types of protein-protein interactions result in different protein-protein interface patterns. The formed pattern of a protein-protein complex interface involves in affinity, stability and specificity of the complex. Protein-protein interfaces may be divided into several subtypes, such as intra-domain (interfaces within one structural domain), domain-domain (interfaces between different domains within one protein chain), homo-oligomer (interfaces between constantly interacting identical protein chains), homo-complex (interfaces between transiently interacting identical protein chains), hetero-oligomer (interfaces between constantly interacting different protein chains) and hetero-complex (interfaces between transiently interacting different protein chains).

The present disclosure provides a compound capable of binding to a druggable protein-protein interface for promoting the therapeutic effects of human diseases and other emerging infectious diseases. Further, the present disclosure provides a pharmaceutical combination that combines two or more drugs or compounds functioned by targeting different groups of residues (sites) in a single target (e.g., a single protein target and a single protein complex target) to achieve an enhanced therapeutic effect while lowering down the dose usage of each individual drug. The drugs in the pharmaceutical combination may target different sites of a target protein complex or on the same target protein for an enhanced inhibition on its biological function.

In at least one embodiment of the present disclosure, the pharmaceutical combination of an active site inhibitor and an interface blocker provided herein may additively or synergistically suppress the COVID-19 virus and facilitate the antiviral drug design from the molecular basis.

In at least one embodiment of the present disclosure, a pharmaceutical combination for suppressing SARS-CoV2 is provided, comprising a first agent capable of binding to a first binding site of a 3C-like main protease ($3CL^{pro}$) complex of the SARS-CoV2, and a second agent capable of binding to a second binding site of the $3CL^{pro}$ complex of the SARS-CoV2, wherein the first binding site and the second binding site are functionally different sites in the three-dimensional structure of the SARS-CoV2 $3CL^{pro}$ complex. In some embodiments, the first binding site and the second binding site are two functionally different sites selected from an orthosteric site, an allosteric site, and an interface site of the SARS-CoV2 $3CL^{pro}$ complex. For example, if the first binding site is an orthosteric site of one subunit of the SARS-CoV2 $3CL^{pro}$ complex, then the second binding site could be an allosteric site of another subunit of the SARS-CoV2 $3CL^{pro}$ complex, or an interface site between the two subunits of the SARS-CoV2 $3CL^{pro}$ complex.

In exemplary embodiments of the pharmaceutical combination of the present disclosure, the SARS-CoV2 $3CL^{pro}$ complex may be a complex of two SARS-CoV2 $3CL^{pro}$ monomers (i.e., a SARS-CoV2 $3CL^{pro}$ homodimer), a complex of a SARS-CoV2 $3CL^{pro}$ monomer and a substrate thereof, and a complex of a SARS-CoV2 $3CL^{pro}$ homodimer and a substrate thereof. In some embodiments, the SARS-CoV2 $3CL^{pro}$ complex is in a homodimeric form, and the second agent blocks at a dimerization interface of the SARS-CoV2 $3CL^{pro}$ homodimer.

In exemplary embodiments of the pharmaceutical combination of the present disclosure, the first agent and the second agent provide at least one of a synergistic effect and an additive effect for suppressing the SARS-CoV2.

In exemplary embodiments of the pharmaceutical combination of the present disclosure, the first binding site is an orthosteric site of the SARS-CoV2 $3CL^{pro}$ complex.

In exemplary embodiments of the pharmaceutical combination of the present disclosure, the second binding site is an allosteric site of the SARS-CoV2 $3CL^{pro}$ complex. In some embodiments, the second binding site is located at an interface of domain II and N terminus of the SARS-CoV2 $3CL^{pro}$ complex.

In at least one embodiment of the pharmaceutical combination of the present disclosure, the first agent and the second agent may be independently a drug-like compound (also referred to as a "compound" herein) or a repurposed FDA-approved drug (also referred to as a "drug" herein). In some embodiments, the pharmaceutical combination provided herein for targeting different sites may be a combination of a compound or a drug, or a combination of compounds or drugs.

In exemplary embodiments of the pharmaceutical combination of the present disclosure, the first agent and the second agent are independently selected from the group consisting of an FDA-approved drug, an FDA-approved biologic, a drug metabolite, a prodrug, a small molecular compound, an experimental small molecule, an experimental biologic, an experimental polypeptide, and any combination thereof.

In exemplary embodiments of the pharmaceutical combination of the present disclosure, the first agent is one selected from boceprevir, telaprevir, and nelfinavir.

In exemplary embodiments of the pharmaceutical combination of the present disclosure, the second agent is an antibiotic or an antifungal agent. In some embodiments, the second agent is norvancomycin.

In exemplary embodiments of the pharmaceutical combination of the present disclosure, the first agent and the second agent are in separate compositions or in a single composition.

In exemplary embodiments of the pharmaceutical combination of the present disclosure, the second agent has an amount higher than an amount of the first agent. In some embodiments, the amount of the second agent is at least 10 times higher than the amount of the first agent.

In exemplary embodiments of the pharmaceutical combination of the present disclosure, the amount of the first agent is from 1 nanomolar (nM) to 50 micromolar (μM), such as about 1 nM, 5 nM, 10 nM, 20 nM, 50 nM, 80 nM, 100 nM, 250 nM, 500 nM, 750 μM, 1 μM, 2 μM, 3 μM, 4 μM, 5 μM, 10 μM, 15 μM, 20 μM, 25 μM, 30 μM, 35 μM, 40 μM, 45 μM, or 50 μM.

In exemplary embodiments of the pharmaceutical combination of the present disclosure, the amount of the first agent is from 0.1 mg/kg to 10 mg/kg, such as about 0.1 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, or 10 mg/kg.

In exemplary embodiments of the pharmaceutical combination of the present disclosure, the amount of the second agent is from 1 nM to 100 μM, such as about 1 nM, 5 nM, 10 nM, 20 nM, 50 nM, 80 nM, 100 nM, 250 nM, 500 nM, 750 nM, 1 μM, 5 μM, 10 μM, 12.5 UM, 15 μM, 30 μM, 37.5 μM, 50 μM, 60 μM, 65 μM, 70 μM, 80 μM, 85 μM, 90 μM, 95 μM, or 100 μM.

In exemplary embodiments of the pharmaceutical combination of the present disclosure, the amount of the second agent is from 0.1 mg/kg to 10 mg/kg, such as about 0.1 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, or 10 mg/kg.

In exemplary embodiments, the pharmaceutical combination of the present disclosure brings about a superior effect than the respective use of a single active component in the pharmaceutical combination for suppressing the SARS-CoV2.

The present disclosure also provides a method for treating a SARS-CoV2 $3CL^{pro}$-related disease in a subject in need thereof, comprising administering to the subject an effective amount of a first agent capable of binding to a first binding site of a SARS-CoV2 $3CL^{pro}$ complex, and an effective amount of a second agent capable of binding to a second binding site of the SARS-CoV2 $3CL^{pro}$ complex, wherein the first binding site and the second binding site are functionally different sites in the three-dimensional structure of the SARS-CoV2 $3CL^{pro}$ complex.

In exemplary embodiments of the method of the present disclosure, the SARS-CoV2 $3CL^{pro}$ complex may be a complex of two SARS-CoV2 $3CL^{pro}$ monomers (i.e., a SARS-CoV2 $3CL^{pro}$ homodimer), a complex of a SARS-CoV2 $3CL^{pro}$ monomer and a substrate thereof, and a complex of a SARS-CoV2 $3CL^{pro}$ homodimer and a substrate thereof. In some embodiments, the SARS-CoV2 $3CL^{pro}$ is in a homodimeric form, and the second agent blocks a dimerization interface of the SARS-CoV2 $3CL^{pro}$ homodimer.

In exemplary embodiments of the method of the present disclosure, the first agent and the second agent provide at least one of a synergistic effect and an additive effect for treating the SARS-CoV2 3CL$^{pro}$-related disease.

In exemplary embodiments of the method of the present disclosure, the first binding site is an orthosteric site of the SARS-CoV2 3CL$^{pro}$ complex.

In exemplary embodiments of the method of the present disclosure, the second binding site is an allosteric site of the SARS-CoV2 3CL$^{pro}$ complex. In some embodiments, the second binding site is located at an interface of domain II and N terminus of the SARS-CoV2 3CL$^{pro}$ complex.

In exemplary embodiments of the method of the present disclosure, the first agent is one selected from boceprevir, telaprevir, and nelfinavir.

In exemplary embodiments of the method of the present disclosure, the second agent is an antibiotic or an antifungal agent. In some embodiments, the second agent is norvancomycin.

In exemplary embodiments of the method of the present disclosure, the first agent and the second agent are administered concurrently, separately or sequentially to the subject.

In exemplary embodiments of the method of the present disclosure, the first agent and the second agent are administered concurrently in separate compositions to the subject.

In exemplary embodiments of the method of the present disclosure, the first agent and the second agent are administered concurrently as a single composition to the subject.

In exemplary embodiments of the method of the present disclosure, the SARS-CoV2 3CL$^{pro}$-related disease is COVID-19.

In this disclosure, where a document, act or item of knowledge is referred to or discussed, this reference or discussion is not an admission that the document, act or item of knowledge or any combination thereof was at the priority date, publicly available, known to the public, part of common general knowledge, otherwise constitutes prior art under the applicable statutory provisions, or is known to be relevant to an attempt to solve any problem with which this specification is concerned.

BRIEF DESCRIPTION OF THE DRAWINGS

For a full understanding of this disclosure, reference should be made to the following detailed descriptions, taken in connection with the accompanying drawings.

FIG. 3A indicates molecular dynamics (MD) snapshot at 0 ns, and FIG. 3B indicates MD snapshot at 10 ns. The blue and red colors indicate the domain II interface (SER121, PRO122, SER123, GLY124, VAL125, SER139, PHE140, LEU141 and GLU166) and N-terminus interface residues (SER1, GLY2, ARG4, MET6, ALA7 and PRO9), respectively, and the active site residues are shown in a ball-and-stick model.

DETAILED DESCRIPTION

Figure 1:
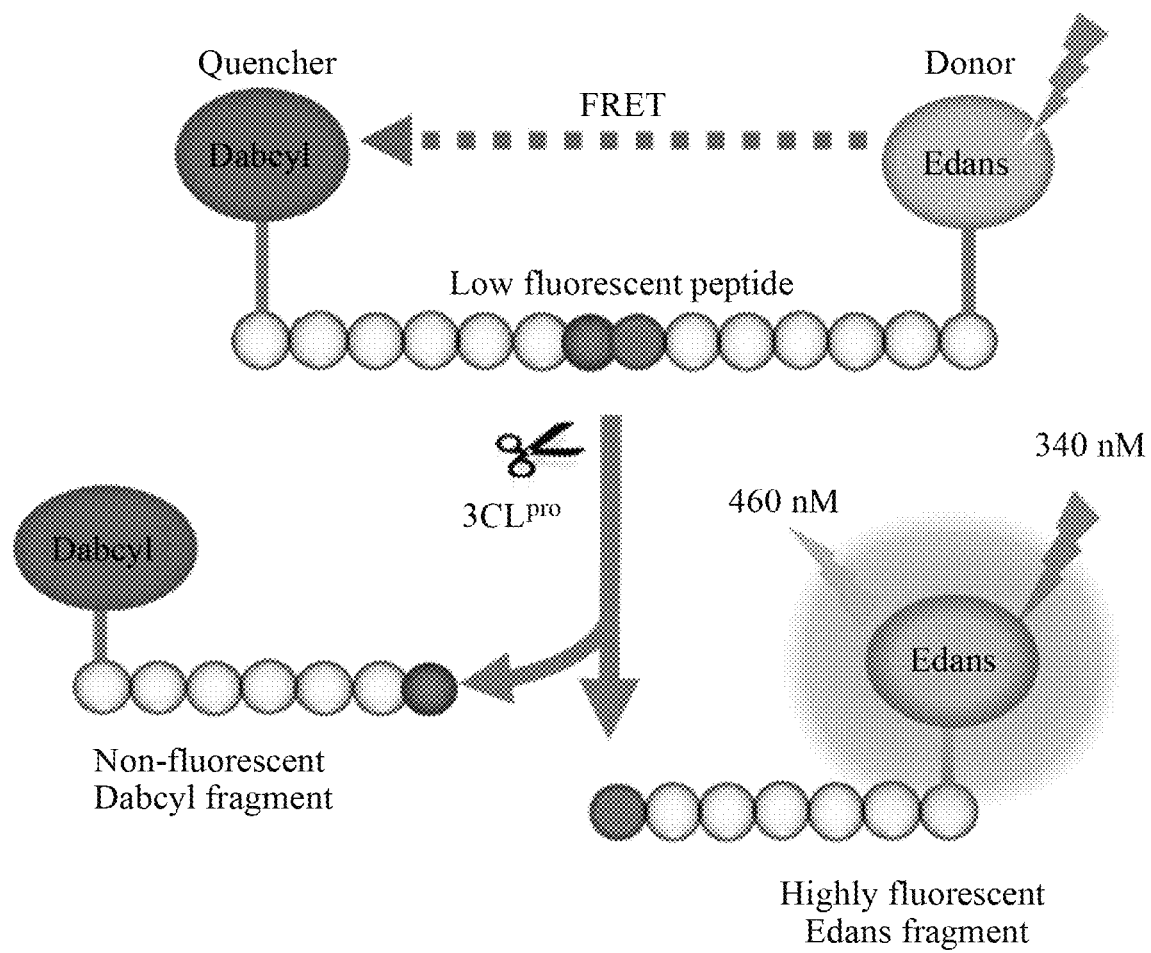
FIG. 1 is a scheme of the fluorogenic 3CL$^{pro}$ protease enzymatic assay. The fluorescence of Edans in the C-terminal of the peptide substrate (Dabcyl-KTSAVLQSGFRKME-Edans, the cleavage site is in between the amino acids Q and S) is quenched by the Dabcyl in the N-terminus without the 3CL$^{pro}$ enzymatic cleavage. After the protease is added and cleaves the peptide substrate, the quencher molecule Dabcyl can no longer quench the fluorophore Edans which results in an increase in fluorescence emission at 460 nm. The intensity of this fluorescence is proportional to the protease activity. FRET: fluorescence resonance energy transfer.

In the following description of the embodiments, reference is made to the accompanying drawings, which form a part thereof, and within which are shown by way of illustrative embodiments by which the disclosure may be practiced. It is to be understood that other embodiments may also be utilized, and structural changes may be made without departing from the scope of the disclosure.

As used in this disclosure, the singular forms "a," "an," and "the" include plural referents unless the content clearly dictates otherwise. As used herein, the term "and" is intended to be inclusive unless otherwise indicated. As used herein, the term "or" is generally employed in its sense including "and/or" unless the context clearly dictates otherwise.

As used herein, the term "about" when referring to the numerical value is meant to encompass variations of ±20%, ±10%, ±5%, ±1%, ±0.5%, or ±0.1% from the numerical value. Such variations in the numerical value may occur by, e.g., the experimental error, calculation errors, routin minor adjustments, the typical error in measuring or handling procedure for making compounds, compositions, concentrates, or formulations, the differences in the source, manufacture, or purity of starting materials or ingredients used in the present disclosure, or like considerations.

As used herein, the terms "comprising," "having," "including," and "containing" are to be construed as open-ended terms (i.e., meaning "including, but not limited to") unless otherwise noted.

As used herein, the terms "composition" and "composite" may be used interchangeably.

As used herein, the term "treating" or "treatment" refers to obtaining a desirable pharmacologic and/or physiologic effect, e.g., inhibition of viral entry and/or replication in a host. The effect may be prophylactic in terms of completely or partially preventing a disease or symptoms or conditions thereof, or may be therapeutic in terms of completely or partially curing, alleviating, relieving, remedying, or ameliorating a disease or an adverse effect attributable to the disease or symptoms or conditions thereof.

As used herein, the terms "patient," "individual" and "subject" are used interchangeably. The term "subject" means a human or animal. Examples of the subject include, but are not limited to, human, monkey, mice, rat, woodchuck, ferret, rabbit, hamster, cow, horse, pig, deer, dog, cat, fox, wolf, chicken, emu, ostrich, and fish. In some embodiments of the present disclosure, the subject is a mammal, e.g., a primate such as a human.

As used herein, the phrase "an effective amount" refers to the amount of an active agent that is required to confer a desired therapeutic effect on a subject in need thereof (e.g., reducing the amount of viruses in a host). Effective doses may vary, as recognized by those skilled in the art, depending on routes of administration, excipient usage, the possibility of co-usage with other therapeutic treatment, and the condition to be treated.

As used herein, the term "administering" or "administration" refers to the placement of an active agent into a subject by a method or route which results in at least partial localization of the active agent at a desired site to produce the desired effect. The active agent described herein may be administered by any appropriate route known in the art.

The numeral ranges used herein are inclusive and combinable, any numeral value that falls within the numeral scope herein could be taken as a maximum or minimum value to derive the sub-ranges therefrom. For example, it should be understood that the numeral range "0.1 mg/kg to 10 mg/kg" comprises any sub-ranges between the minimum value of 0.1 mg/kg to the maximum value of 10 mg/kg, such as the sub-ranges from 0.1 mg/kg to 2 mg/kg, from 5 mg/kg to 10 mg/kg, from 4 mg/kg to 8 mg/kg and so on. In addition, a plurality of numeral values used herein can be optionally selected as maximum and minimum values to derive numerical ranges. For instance, the numerical ranges of 0.1 mg/kg to 5 mg/kg, 0.1 mg/kg to 10 mg/kg, and 5 mg/kg to 10 mg/kg can be derived from the numeral values of 0.1 mg/kg, 5 mg/kg, and 10 mg/kg.

The materials and processes used in the present disclosure will be provided and described in detail below.

Molecular Dynamics (MD) Simulation and Molecular Mechanics Generalized Born Surface Area (MM/GBSA)

The MD simulations for user-selected poses were performed using the OpenMM package in an explicit solvent. The simulation system of the user-selected protein target-drug binding pose complex was prepared using the LEaP program in AmberTools. The complex was solvated in an explicit solvent of the transferable intermolecular potential 3P (TIP3P) water model with at least 10 Å of a water layer between each side of the cube to the protein target. Sodium and chloride ions were used to neutralize the system and achieved a salt concentration of 0.1 M. The system was first energy minimized for all the hydrogen, water, and ion positions, with the remaining atoms restrained using a force constant of 10 kcal/mol/Å$^2$, and then for atoms also including protein heavy atoms, with the protein C-alpha atoms and drug heavy atoms restrained using a force constant of 2 kcal/mol/Å$^2$. The system was then heated to 320 K in NVT (or canonical) ensemble for 100 ps and equilibrated for another 110 ps in NPT (or isothermal-isobaric) ensemble 310 K and 1 atm. The protein C-alpha atoms and drug heavy atoms were weakly restrained (0.1 kcal/mol/Å$^2$) during the heating and equilibration. The equilibrated system was then subject to 10 ns simulation using the same condition as in the equilibration except the removing of all restraints, and the snapshots were sampled for every 0.1 ns, resulting in a trajectory composed of 100 frames. Langevin dynamics with a collision frequency of 2 ps$^{-1}$ and a Monte Carlo Barostat with the volume rescaled every 25 timesteps were applied for temperature and pressure controls, respectively. Particle mesh Ewald (PME) method was used to calculate the energy of non-bonded interaction with 10 Å as the distance cutoff. The water molecules were treated rigid, and all the bonds involving hydrogens were constrained. The binding free energy between the target protein and drugs for each sampled snapshot was calculated by MM/GBSA methods with molecular mechanics Poisson-Boltzmann surface area (MMPBSA.py) tools come with AmberTools. The simulated drug was assigned a higher rank if it had a favorable binding free energy averaged on all the sampled snapshots and did not leave the binding pocket (the distance of the center of mass of drug's heavy atoms to that in the docked drug pose >10 Å) in the simulation. All the processing and analysis of the docking poses and MD trajectories were performed with the aids of ParmEd, Cpptraj, PyTraj, and MDAnalysis.

System Preparation and Defining of the Interface Residues

Protein targets were prepared by performing a molecular dynamics (MD) simulation of 200 ns starting from the homodimer 3CL$^{pro}$ (PDB ID: 6Y2E). Consequently, the chain A of the last frame was extracted and performed additional 100 ns simulation. Finally, the last frame of the simulation (End of Monomer Simulation) was termed EMS. The EMS monomer served as the target conformation for screening the interface drug (by global docking using Autodock Vina).

To find drugs blocking the combination of two monomers, the interface residue of the homodimer was first defined by the contact number where a contact was the atom-atom distance smaller than or equal to 4 Å. The interface residues of the 3CL$^{pro}$ homodimer were defined by the contact number of a residue larger than six. Nine interfacial residues in the domain II, SER121, PRO122, SER123, GLY124, VAL125, SER139, PHE140, LEU141, and GLU166, and six residues in the N-terminus, SER1, GLY2, ARG4, MET6, ALA7, and PRO9, could be found.

The Global Docking and Drug Cluster Analysis

AutoDock Vina was used for drug screening, where each of the 2016 FDA-approved drugs was docked in the protein and sampled for 20 poses. The docking box was set to cover the whole structure of the protein target with an additional 5 Å margin patched on each side of the docking box. Exhaustiveness of 20 was set to give comprehensive screening results. The procedure was termed as the global docking. Consequently, the global docking was used on the EMS structure, and the output docking poses were submitted to further drug clustering analysis.

Considering that the contribution of conformational entropy could facilitate the binding free energy, the poses of global docking were clustered for each drug by the hierarchical clustering method. The number of poses in each cluster for each drug was calculated, and the number of poses in the largest cluster was termed as the largest cluster size (LCS). The mean LCS of all the FDA drugs was termed MLCS. The drugs whose LCS were smaller than or equal to the rounded MLCS were removed. The remaining drugs were served as candidate drugs for further drug contact analysis.

The Drug Contact Analysis

Interface drugs having high contact with domain II and N-terminus were chosen. A contact was formed if a heavy atom in the drug was <4 Å from a heavy atom of interface residues defined in the above section. The top 50 drugs having the highest contact number were selected for further MD simulations and MM/PB (GB) SA analysis.

Fluorescence Resonance Energy Transfer (FRET)-Based $3CL^{pro}$ Enzyme Activity Assay The FRET-based assay was designed for $3CL^{pro}$ activity assay and explained in FIG. 1. The $3CL^{pro}$ enzyme assay was developed in a 96-well black microplate with a total volume of 50 µL. 30 µL of 0.5 ng/µL enzyme in a reaction buffer was added into each well, followed by the addition of 10 µL substrate solution to a final concentration of 40 µM. Enzymatic reaction gave fluorescence whose intensity was measured after incubation for 4 hours at 37° C. with slow shaking in a microtiter plate reading fluorimeter (BioTek Synergy HTX multi-mode reader, VT, US) with Ex=340 nm/Em=460 nm.

Virus Isolate and Plaque Reduction Assay

Sputum specimen obtained from a SARS-CoV2-infected Taiwanese patient was propagated in Vero E6 cells in Gibco Dulbecco's modified Eagle medium (DMEM) supplemented with 2 µg/mL tosylsulfonyl phenylalanyl chloromethyl ketone (TPCK)-trypsin (Sigma-Aldrich). Culture supernatant was harvested when cytopathic effects (CPE) were seen in more than 70% of cells, and viral titers were determined by a plaque assay. The SARS-CoV2 isolate used herein is hCoV-19/Taiwan/NTU13/2020 (Accession ID: EPI_ISL_422415).

Plaque reduction assay was performed to determine the antiviral activity of test compounds. Briefly, Vero E6 cells were seeded to the 6-well culture plate in DMEM with 10% fetal bovine serum (FBS) and antibiotics one day before infection. Vero E6 cells were infected by SARS-CoV2 virus (50 to 100 plaque forming unit, pfu) for 1 hour at 37° C. After removal of virus inoculum, the cells were washed once with phosphate buffered saline (PBS) and overlaid with 1 mL medium containing test compounds at indicated concentration and 1% methylcellulose for 5 days at 37° C. After 5 days, the cells were fixed with 10% formalin overnight. After removal of overlay media, the cells were stained with 0.5% crystal violet, and the plaques were counted. The percentage of inhibition was calculated as $[1-(V_D/V_C)] \times 100\%$, where $V_D$ and $V_C$ refer to the virus titer in the presence and absence of the inhibitors, respectively. The minimal concentrations of compounds required to reduce 50% of plaque numbers ($EC_{50}$) were calculated by regression analysis of the dose-response curves generated from plaque assays. For each data point, the measurements were repeated three times to yield the averaged number, standard deviations and standard errors.

Cytotoxicity Assay

Cytotoxicity assay was performed using Vero E6 cells described above to determine the cytotoxicity of tested compounds, i.e., norvancomycin and nelfinavir. DMSO, the solvent used to help fully dissolve the drugs of interest, was used as the negative control. The percentage of cell survival and 50% cytotoxic concentration ($CC_{50}$) were derived.

The following examples provide various non-limiting embodiments and properties of the present disclosure.

Example 1: The Interface Blocker of $3CL^{pro}$

Figure 2:
FIG. 2 shows the homodimer structure of 3CL$^{pro}$. The N-terminus (residue 1-9), domain I (residue 10-98), domain II (residue 100-181), and domain III (residue 198-302) are shown in thickened red tube, orange, blue and ice blue, respectively. One of the monomers in the front is shown in transparent white. The catalytic residues HIS41 and CYS145 are represented in a ball-and-stick model.

FIG. 2 illustrated a homodimer structure of $3CL^{pro}$, where the three domains were labeled by different colors. The dimer interface was located between the domain II of one monomer and N-terminus in another monomer. The MD simulations provided a more physiologically realistic environment than the environment (in vacuum), wherein small-molecule docking was conducted. The mean drug-interface contacts derived from MD simulations could provide a guideline for drug screening. Based on the global docking and drug contact analysis, drug-interface contacts for the domain II and for the N-terminus were calculated, where a drug having a higher drug-interface contact could suggest higher interaction-interference caused by the drug. Table 1 below showed examples of top-10 drugs ranked by drug-interface contact for both interfaces.

TABLE 1

The top-10 drugs ranked by drug-interface contact for both interfaces

| | Drug ID | Drug name | Domain II contact | | Drug ID | Drug name | N-terminus contact |
|---|---|---|---|---|---|---|---|
| 1 | 02006 | Icatibant | 37 | 1 | 02009 | Norvancomycin | 34 |
| 2 | 02009 | Norvancomycin | 36 | 2 | 02011 | Fondaparinux | 31 |
| 3 | 01684 | Kanamycin | 35 | 3 | 02006 | Icatibant | 31 |
| 1 | 00849 | Warfarin | 35 | 4 | 01973 | Ombitasvir | 29 |
| 5 | 00452 | Pidotimod | 35 | 5 | 01982 | Carbetocin | 28 |
| 6 | 00622 | Tolcapone | 35 | 6 | 01067 | Raltitrexed | 28 |
| 7 | 00042 | Pyrazinamide | 35 | 7 | 01916 | Ritonavir | 28 |
| 8 | 02012 | Daptomycin | 33 | 8 | 01693 | Dasatinib | 27 |
| 9 | 00060 | Allopurinol | 33 | 9 | 01574 | Bictegravir | 27 |
| 10 | 00212 | Dacarbazine | 32 | 10 | 01951 | Glycyrrhizic acid | 26 |

Further, not only top-10 drugs but top-50 drugs ranked by drug-interface contacts were selected to perform the MD simulation and MM/PB (GB) SA analysis using the standard protocol. From the simulation trajectory, the mean drug-interface contacts were calculated by the average drug-interface contacts over the snapshots of the last 2 ns of MD between the 3CL$^{pro}$ interface and drugs. Top-10 drugs ranked by mean drug-interface contacts were selected for each interface as shown in Tables 2 and 3.

Table 2 and Table 3 below showed the mean drug-interface contacts between drug and domain II/N-terminus, and corresponding MD-based energy. The "Contact" referred to the mean drug-interface contacts calculated over the snapshots of last 2 ns of MD trajectories. The column MMG(P)BSA was the MMG(P)BSA-derived energy in the unit of kcal/mol. It was observed that top-10 drugs ranked by drug-interface contacts shown in Table 1 may not be top-10 when the ranking was based on the mean drug-interface contacts, and generally, drugs with high mean drug-interface contacts had low MD/MMP(G)BSA derived energy, namely good drug-protein affinity.

TABLE 2

The mean drug-interface contacts between drug and domain-II, and corresponding MD based energy

| | Drug ID | Drug name | Contact | MMGBSA | MMPBSA |
|---|---|---|---|---|---|
| 1 | 01995 | Anidulafungin | 27.80 | −29.71 ± 2.79 | −17.47 ± 5.50 |
| 2 | 00297 | Miglitol | 22.25 | −21.99 ± 3.24 | −19.50 ± 3.05 |
| 3 | 01959 | Spiramycin I | 18.80 | −36.45 ± 5.02 | −19.87 ± 5.54 |
| 4 | 00755 | Alosetron | 18.25 | −33.60 ± 3.52 | −26.32 ± 3.48 |
| 5 | 01987 | Felypressin | 17.55 | −30.34 ± 5.20 | −22.14 ± 4.98 |
| 6 | 00152 | 6-thioguanine | 14.95 | −20.41 ± 3.31 | −14.70 ± 3.45 |
| 7 | 01719 | Taurohyodeoxycholic acid | 14.30 | −44.99 ± 3.80 | −28.29 ± 4.75 |
| 8 | 01988 | Ornipressin | 13.40 | −37.88 ± 4.28 | −31.47 ± 4.48 |
| 9 | 01858 | Gamma-oryzanol | 13.00 | −25.25 ± 2.95 | −22.65 ± 2.31 |
| 10 | 00489 | Lacosamide | 12.70 | −22.72 ± 2.26 | −16.44 ± 2.68 |

TABLE 3

The mean drug-interface contacts between drug and N-terminus, and corresponding MD based energy

| | Drug ID | Drug name | Contact | MMGBSA | MMPBSA |
|---|---|---|---|---|---|
| 1 | 01973 | Ombitasvir | 31.90 | −30.02 ± 2.62 | −22.03 ± 2.66 |
| 2 | 02009 | Norvancomycin | 29.65 | −26.07 ± 3.56 | −18.28 ± 2.54 |
| 3 | 01324 | Lubiprostone | 24.35 | −24.89 ± 2.76 | −18.46 ± 2.80 |
| 4 | 01988 | Ornipressin | 23.80 | −55.73 ± 4.06 | −33.04 ± 5.57 |
| 5 | 02006 | Icatibant | 20.45 | −46.10 ± 5.60 | −29.86 ± 5.47 |
| 6 | 00755 | Alosetron | 20.30 | −29.40 ± 1.57 | −23.98 ± 2.00 |
| 7 | 01991 | Caspofungin | 18.35 | −54.00 ± 3.82 | −37.49 ± 4.48 |
| 8 | 01990 | Plicamycin | 18.20 | −41.53 ± 3.66 | −21.20 ± 3.58 |
| 9 | 01604 | Minocycline | 17.65 | −28.90 ± 3.55 | −16.70 ± 4.87 |
| 10 | 00438 | Telbivudine | 17.40 | −29.28 ± 2.20 | −22.58 ± 2.62 |

Figure 3A:
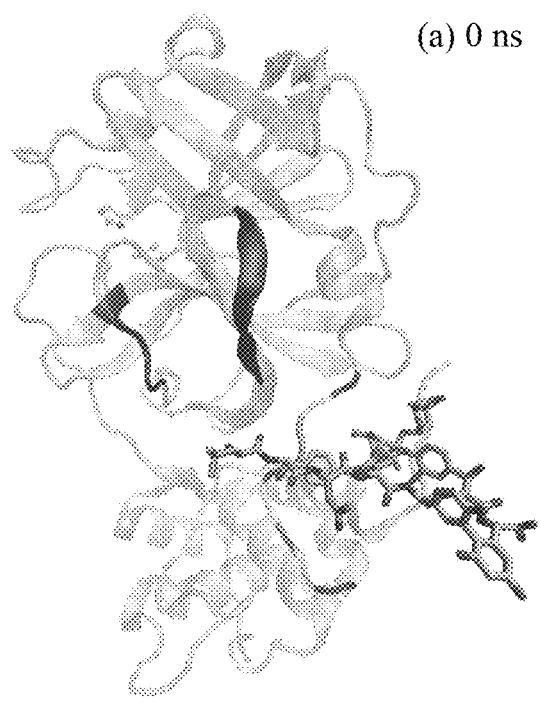
FIGS. 3A and 3B illustrate that norvancomycin contacts with N-terminus interface residues (orange color).
Figure 3B:
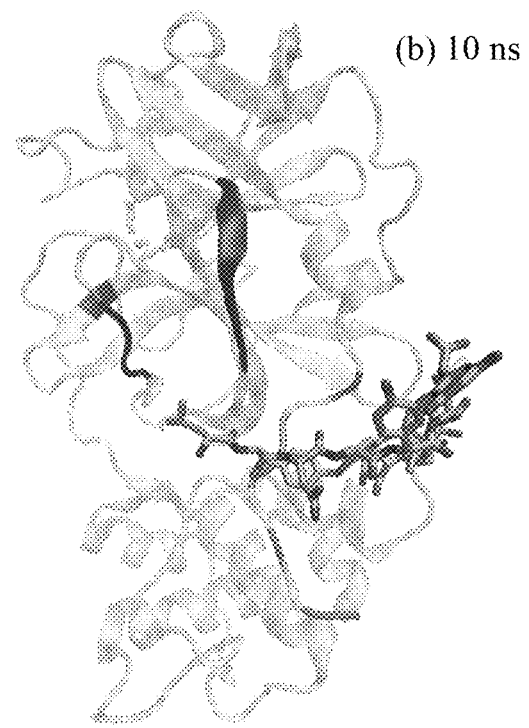

From the above results, the drug norvancomycin (02009) revealed high contacts with the N-terminus (orange color in FIGS. 3A and 3B) in both global docking (rank 1 of Table 1) and MD simulations (rank 2 of Table 3). Further, the MD snapshots shown in FIGS. 3A and 3B demonstrated that norvancomycin tightly bound with the N-terminus interface residues in physiologically realistic environment.

Example 2: Verification of the Interface Blocker Using In Vitro 3C-Like Protease Activity Assay From the top-2 that had the most contact with the domain-II and N-terminus of 3CL$^{pro}$, four interface drugs, namely anidulafungin (01995), miglitol (00297), ombitasvir (01973) and norvancomycin (02009) were obtained, where norvancomycin was the first drug chosen for the following enzyme activity assay.

Figure 4:
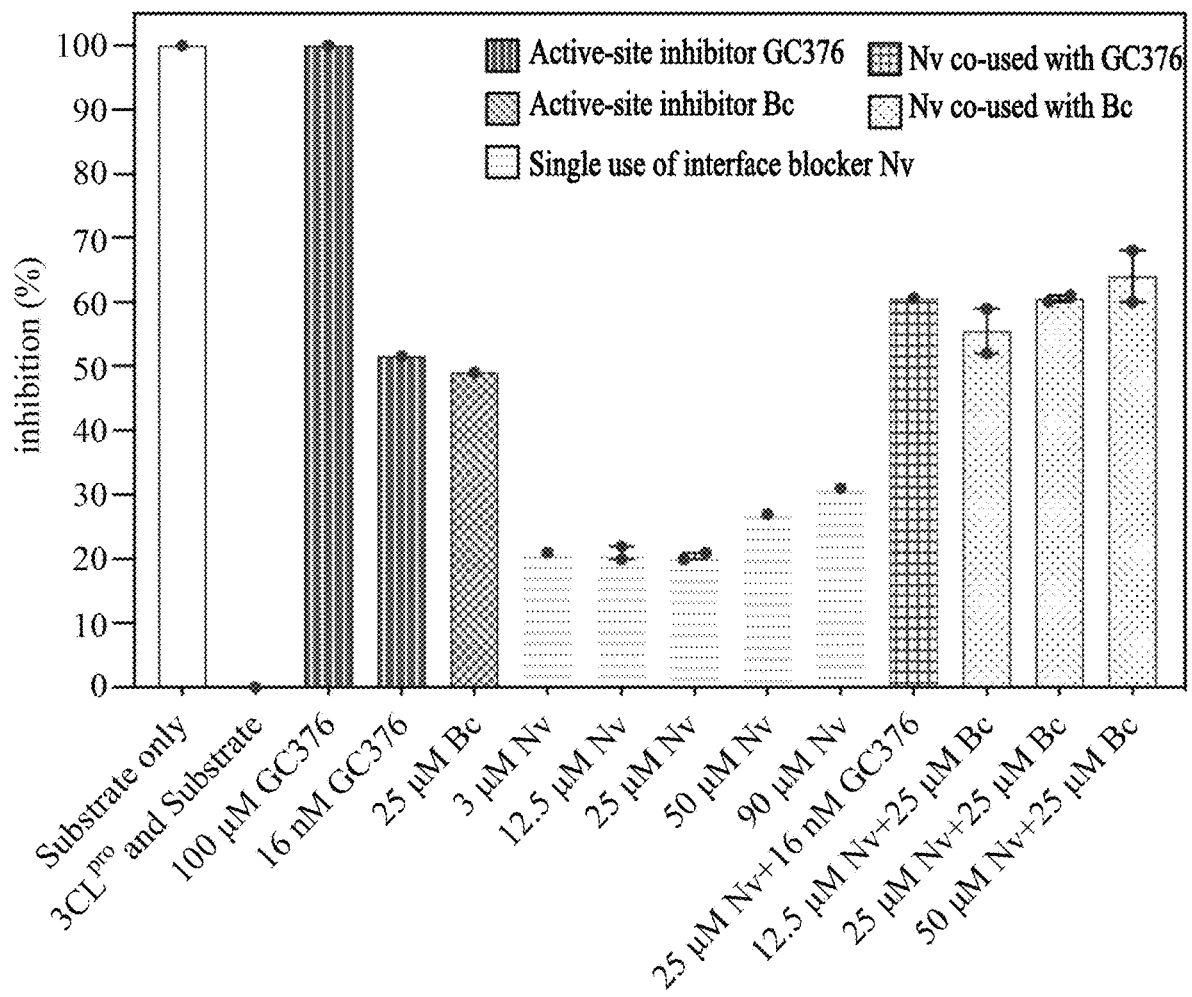
FIG. 4 shows the inhibition in the presence of active site inhibitors and/or the interface blocker, norvancomycin (Nv). 3CL$^{pro}$ inhibition percentage of different test groups is determined by "$(I_{substrate+3CLpro}-I_{test\_group})/(I_{substrate+3CLpro}-I_{substrate})\times 100\%$, where "I" is the observed intensity of blue fluorescence light (at 460 nm); $I_{substrate}$ and $I_{substrate+3CLpro}$ are supposed to give the lowest and the highest intensity, respectively, where the substrate is a peptide labeled by a quencher and fluorophore at its N- and C-termini (as shown in FIG. 1). Specifically, the fluorescence of Edans in the C-terminal of the peptide (Dabcyl-KTSAVLQSGFRKME-Edans; the cleavage site is in between the amino acids Q and S) is quenched by the Dabcyl in the N-terminus in the absence of the 3CL$^{pro}$ enzymatic cleavage. Norvancomycin (Nv) is the interface blocker here while the FDA drugs boceprevir (Bc) and GC376 (in its clinical trials) are the active-site inhibitors. The results are shown by the average value of two replicates.

A 3CL$^{pro}$ (Cat. #78042-1) assay kit (BPS Bioscience, CA, USA) was used for the single use experiment of the norvancomycin, and it showed 20% to 30% inhibition at 3 μM to 90 μM (see the yellow bars in the middle of FIG. 4). For validating the combination effect on an interface blocker, 25 μM boceprevir, a published drug targeted to 3CL$^{pro}$ active site, was combined with norvancomycin at different concentrations from 12.5 μM to 50 μM. The result showed that the predicted interface blocker co-used with the active site inhibitor at the molar ratio of 1:1 elevated the inhibition by around 10%, while 50 μM norvancomycin gave another 17% inhibition in combination with 25 μM boceprevir. In addition, an active-site inhibitor, GC376, which is still in clinical trials, was also used in combination with norvancomycin to validate the combination effect. The result showed that 25 μM norvancomycin (the interface blocker) in combination with 16 nM GC376 (the active site inhibitor) can provide extra 10% inhibition as compared to that by GC376 alone at the same concentration.

Figure 5:
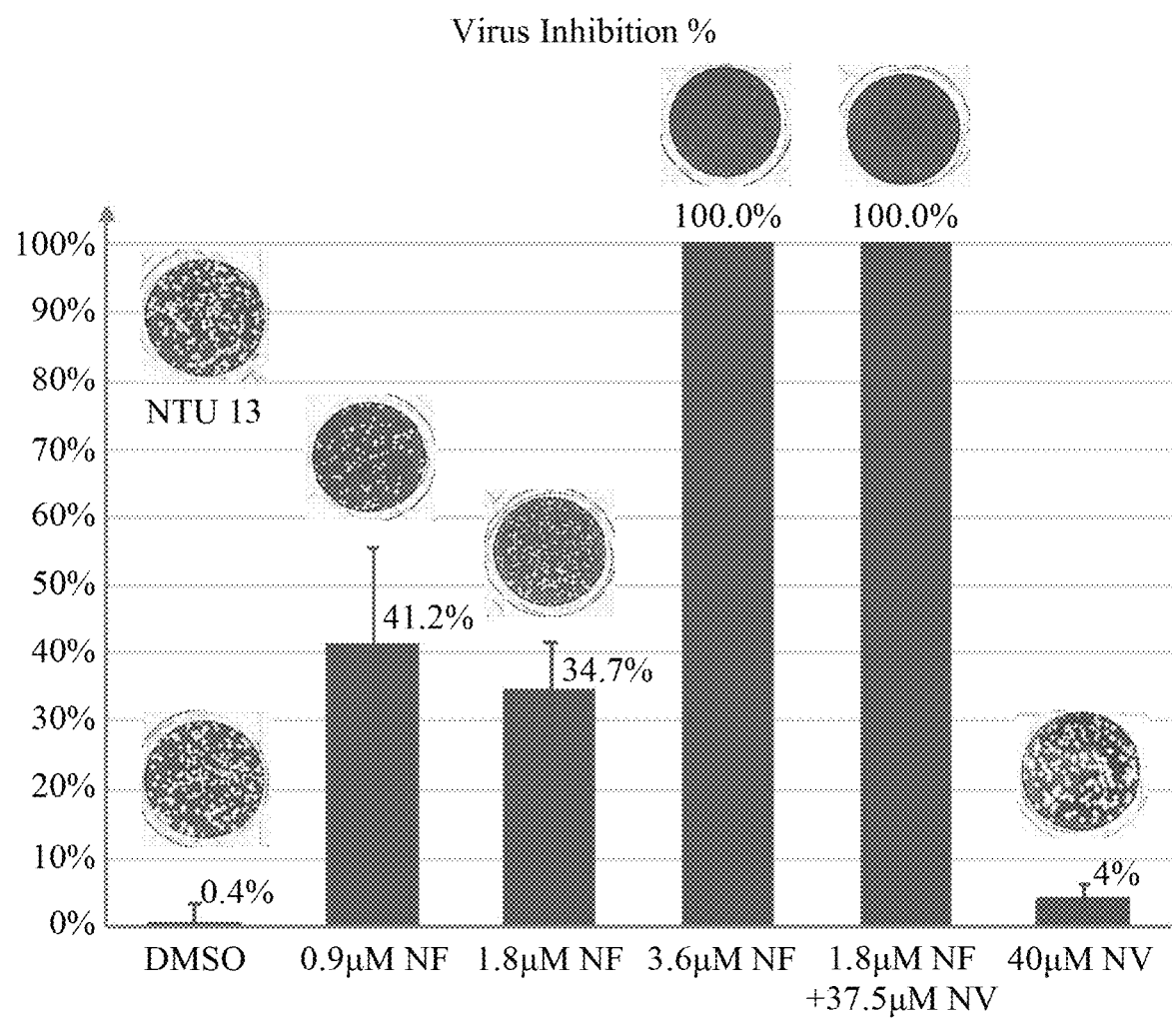
FIG. 5 shows the SARS-CoV2 suppression percentage of the active site inhibitor, nelfinavir (NF), and its co-use with the combined interface blocker, norvancomycin (NV), as well as the suppression percentage of NV only. The percentage of inhibition is calculated as $(V_C-V_D)/V_C\times 100\%$, where $V_D$ and $V_C$ refer to the virus titer (presentative ones) in the presence and absence of the inhibitors, respectively. DMSO indicates dimethyl sulfoxide in the same concentration as that in the 1.8 µM NF±37.5 µM NV group as a mock drug and the negative control. Drug free control in medium only and the DMSO control happen to have the same average number of plaques. NTU 13: hCoV-19/Taiwan/NTU13/2020.

Example 3: Effect of 3CL$^{pro}$ Active Site Inhibitor Combined with Norvancomycin on Suppression of SARS-CoV2 Replication Cell-based virus suppression tests were conducted in the presence of the interface blockers added with the known 3CL$^{pro}$ active site inhibitors (i.e., nelfinavir) (Pathak et al., 2021, ACS Nano, 15, 857-872) at a P3 laboratory in National Taiwan University Hospital. As shown in FIG. 5, 0.9 μM, 1.8 μM and 3.6 μM nelfinavir suppressed 41%, 35% and 100% of the SARS-CoV2 replication, respectively, and 40 μM norvancomycin suppressed 4% of the SARS-CoV2 replication. In addition, when 37.5 μM norvancomycin was added together with 1.8 μM nelfinavir, the virus became 100% suppressed, and the combination of 3.6 μM nelfinavir and 37.5 μM norvancomycin still 100% suppressed the virus growth. These results indicated that norvancomycin could serve as an "adjuvant" for amplifying the effect of 3CL$^{pro}$ active site inhibitors.

Example 4: Cytotoxicity of Norvancomycin (NV) and Nelfinavir (NF)

Figure 6A:
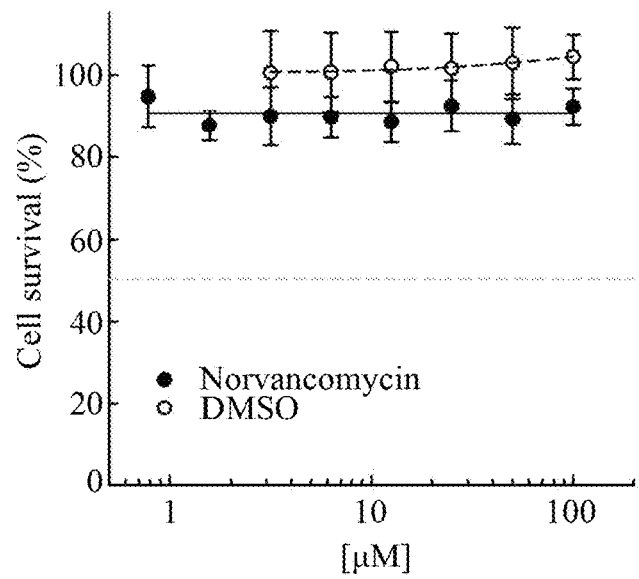
FIGS. 6A and 6B show the cytotoxicity of norvancomycin (NV) and nelfinavir (NF). The percentage of cell survival is determined by obtaining cell viability of Vero E6 cells in the presence of drugs of interest and trace amount of DMSO that help fully dissolve the drug, normalized by Vero E6 cells in the presence of the same concentration of said DMSO, which serves as a control, the cell viability in the absence of the drugs. 50% cytotoxic concentration ($CC_{50}$) represents the concentration of NV and NF required to reduce cell survival by 50%.
Figure 6B:
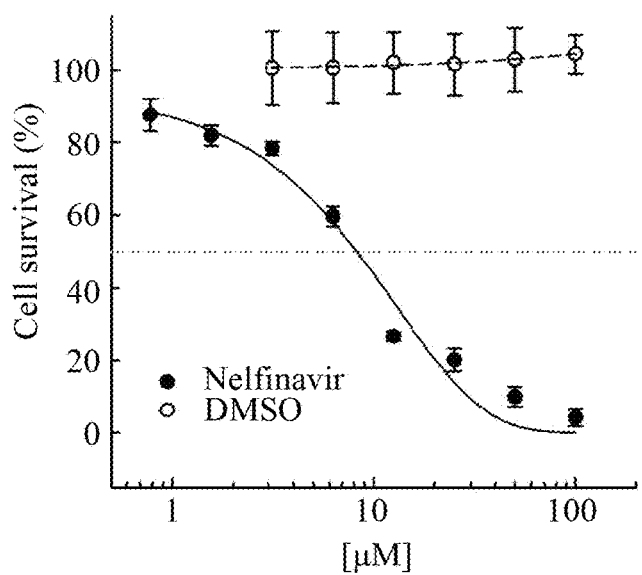

As shown in FIGS. 6A and 6B, CC$_{50}$ of norvancomycin and nelfinavir are >>100 UM and 8.26±0.495 μM, respectively, indicating that norvancomycin has a much lower cytotoxicity as compared to nelfinavir. In addition, cell survival rate under 3.6 μM nelfinavir was 69%, while cell survival rate under 1.8 μM nelfinavir was 84%. According to the results shown in FIGS. 5, 6A, and 6B, it can be seen that by co-administration with norvancomycin, nelfinavir can achieve the 100% suppress effect on the virus growth at lower dosage (1.8 μM) with lower cytotoxicity as that of the higher dosage (3.6 μM) with higher cytotoxicity.

In this disclosure, recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as" and "for example") provided herein, is intended merely to better illuminate the disclosure and does not pose a limitation on the scope of the disclosure unless otherwise indicated.

What is claimed is:

1. A method for treating a SARS-CoV2 3CL$^{pro}$-related disease in a subject in need thereof, comprising administering to the subject an effective amount of a first agent capable of binding to a first binding site of a SARS-CoV2 3CL$^{pro}$ complex, and an effective amount of a second agent capable of binding to a second binding site of the SARS-CoV2 3CL$^{pro}$ complex,
  wherein the first binding site and the second binding site are functionally different sites in a three-dimensional structure of the SARS-CoV2 3CL$^{pro}$ complex,
  wherein the second binding site is located at an interface of domain II and N terminus of the SARS-CoV2 3CL$^{pro}$ homodimer,
  wherein the domain II of the SARS-CoV2 3CL$^{pro}$ homodimer comprises interfacial residues of SER121, PRO122, SER123, GLY124, VAL125, SER139, PHE140, LEU141, and GLU166, and the N-terminus of the SARS-CoV2 3CL$^{pro}$ homodimer comprises interfacial residues of SER1, GLY2, ARG4, MET6, ALA7, and PRO9, and
  wherein the first agent is nelfinavir, and the second agent is Norvancomycin.

2. The method according to claim 1, wherein the first agent and the second agent provide at least one of a synergistic effect and an additive effect for treating the SARS-CoV2 3CL$^{pro}$-related disease.

3. The method according to claim 1, wherein the first binding site is an orthosteric site of the SARS-CoV2 3CL$^{pro}$ complex.

4. The method according to claim 1, wherein the SARS-CoV2 3CL$^{pro}$ complex is in a homodimeric form.

5. The method according to claim 1, wherein the first agent and the second agent are administered concurrently, separately, or sequentially to the subject.

6. The method according to claim 1, wherein the SARS-CoV2 3CL$^{pro}$-related disease is COVID-19.

7. The method of claim 1, wherein the amount of the first agent is between 0.1 mg/kg to 10 mg/kg, and the amount of the second agent is between 0.1 mg/kg to 10 mg/kg.

8. A pharmaceutical combination for suppressing SARS-CoV2, comprising:
  a first agent capable of binding to a first binding site of a SARS-CoV2 3C-like main protease (3CL$^{pro}$) complex; and
  a second agent capable of binding to a second binding site of the SARS-CoV2 3CL$^{pro}$ complex,
  wherein the first binding site and the second binding site are functionally different sites in a three-dimensional structure of the SARS-CoV2 3CL$^{pro}$ complex,
  wherein the second binding site is located at an interface of domain II and N terminus of the SARS-CoV2 3CL$^{pro}$ homodimer,
  wherein the domain II of the SARS-CoV2 3CL$^{pro}$ homodimer comprises interfacial residues of SER121, PRO122, SER123, GLY124, VAL125, SER139, PHE140, LEU141, and GLU166; and the N-terminus of the SARS-CoV2 3CL$^{pro}$ homodimer comprises interfacial residues of SER1, GLY2, ARG4, MET6, ALA7, and PRO9, and
  wherein the first agent is nelfinavir, and the second agent is Norvancomycin.

9. The pharmaceutical combination according to claim 8, wherein the first agent and the second agent provide at least one of a synergistic effect and an additive effect for suppressing the SARS-CoV2.

10. The pharmaceutical combination according to claim 8, wherein the first binding site is an orthosteric site of the SARS-CoV2 3CL$^{pro}$ complex.

11. The pharmaceutical combination according to claim 8, wherein the SARS-CoV2 3CL$^{pro}$ complex is in a homodimeric form.

12. The pharmaceutical combination according to claim 8, wherein the second agent has an amount higher than an amount of the first agent.

13. The pharmaceutical combination according to claim 8, wherein the first agent has an amount of from 1 nanomolar to 50 micromolar.

14. The pharmaceutical combination according to claim 8, wherein the second agent has an amount of from 1 nanomolar to 100 micromolar.

15. The pharmaceutical combination according to claim 8, wherein the first agent has an amount of from 0.1 mg/kg to 10 mg/kg, and the second agent has an amount of from 0.1 mg/kg to 10 mg/kg.

16. The pharmaceutical combination according to claim 8, wherein the first agent and the second agent are in separate compositions.

17. The pharmaceutical combination according to claim 8, wherein the first agent and the second agent are in a single composition.

* * * * *